United States Patent [19]

Leichnitz

[11] 4,294,583
[45] Oct. 13, 1981

[54] HIGHLY SENSITIVE GAS MEASURING METHOD FOR THE ANALYSIS OF BREATH ALCOHOL CONCENTRATIONS, USING TEST TUBES

[75] Inventor: Kurt Leichnitz, Grosse Grönau, Fed. Rep. of Germany

[73] Assignee: Drägerwerk Aktiengesellschaft, Fed. Rep. of Germany

[21] Appl. No.: 125,978

[22] Filed: Feb. 29, 1980

[30] Foreign Application Priority Data

Mar. 31, 1979 [DE] Fed. Rep. of Germany ....... 2912967

[51] Int. Cl.³ ..................... G01N 31/12; G01N 31/22
[52] U.S. Cl. .................................. 23/232 R; 23/907; 73/23; 422/85; 422/86
[58] Field of Search .......... 23/232 R, 230 M, 230 PC, 23/907; 422/83-85, 86; 73/23

[56] References Cited

U.S. PATENT DOCUMENTS

| | | | |
|---|---|---|---|
| 2,795,223 | 6/1957 | Stampe | 422/84 |
| 3,312,527 | 4/1967 | McConnaughey | 422/86 X |
| 3,544,273 | 12/1970 | McConnaughey | 422/85 |
| 3,567,385 | 3/1971 | Van Hall | 23/230 PC |
| 3,698,869 | 10/1972 | Condon | 23/230 PC |
| 3,765,842 | 10/1973 | Purt | 23/232 R |
| 4,040,783 | 8/1977 | Collin | 23/232 R |

Primary Examiner—Michael S. Marcus
Attorney, Agent, or Firm—McGlew and Tuttle

[57] ABSTRACT

A method of testing a person's breath for the purpose of determining the alcohol content of the breath as an indication of the alcohol in the person's blood and using a carbon monoxide gas detector comprises treating the breathing air to oxidize the alcohol of the person's breath-air into carbon monoxide, collecting a predetermined quantity of the carbon monoxide with the treated breathing air and passing the treated quantity through the carbon monoxide detector to determine the quantity of carbon monoxide as an indicator of the alcohol content. The apparatus advantageously include a pyrolysis oven through which the breathing air is directed to oxidize the alcohol into carbon monoxide. The oven is connected to a collector to collect the predetermined quantity of the breathing air and the collector in turn is thereafter connected to a carbon monoxide testing tube. The carbon monoxide formed together with the treated breathing air is drawn from the collector by a suction pump and passed through the carbon monoxide testing tube.

3 Claims, 2 Drawing Figures

U.S. Patent
Oct. 13, 1981
4,294,583
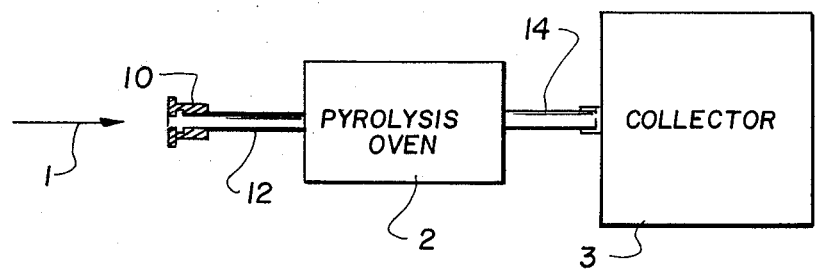
FIG. 1
FIG. 2
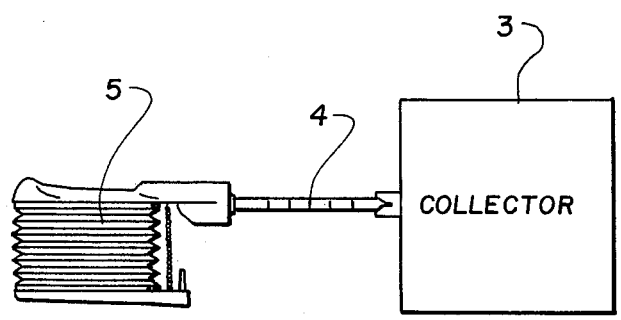

HIGHLY SENSITIVE GAS MEASURING METHOD FOR THE ANALYSIS OF BREATH ALCOHOL CONCENTRATIONS, USING TEST TUBES

FIELD AND BACKGROUND OF THE INVENTION

This invention relates in general to gas detection devices and in particular to a new and useful method and device for testing a person's breath for the purpose of ascertaining the alcohol content of the breath and also the person's blood.

The known colorimetric test tubes for the analysis of the alcohol content in breath have a measuring range from 100 up to 3000 ppm. The lower sensitivity limit is determined by the reagent systems chromate/sulfuric acid on inert reagent carrier used for the alcohol test tubes (Test Tube Pocket Book, Air Testing and Technical Gas Analysis with Dräger Tubes, page 32).

The breath alcohol content is determined from the blood alcohol content. For example, on the basis of the vapor pressure of alcohol over aqueous solutions, a blood alcohol concentration of 0.1% will yield a figure of about 250 ppm ($\cong$ 0.025% by volume). The lower sensitivity limit of the known test tube is already reached at a blood alcohol concentration of 0.05%, i.e. a breath alcohol concentration of about 125 ppm.

SUMMARY OF THE INVENTION

The invention provides a method which makes it possible to reliably determine far smaller blood alcohol/breath alcohol concentrations, using test tubes.

According to the inventive method highly sensitive gas measuring is provided for the analysis of breath alcohol concentrations using test tubes. With the inventive method, exhaled breath is conducted through a pyrolysis oven in which the alcohol oxidizes to carbon monoxide and is then passed with the treated breath into a collector in order to accumulate a predetermined quantity thereof. The collected quantity is then conducted through a known colorimetic carbon monoxide test tube by means of a known air pump.

The advantages achieved by the invention are, in particular, that it is possible to measure reliably blood alcohol concentrations far below 0.05%. The example leads to a measured value corresponding to a blood alcohol concentration of 0.001%. This means a sensitivity greater by the factor 50 when compared to the hitherto known use of alcohol test tubes.

The CO level present in the exhaled breath of smokers can be determined by a direct CO measurement in the breath ahead of the pyrolysis oven and can then be taken into consideration in the alcohol analysis.

Accordingly, it is an object of the invention to provide a method of testing a person's breath for the purpose of determining its alcohol content as an indication of the alcohol in the person's blood and using a CO gas detector, comprising treating the breathing air to oxidize the alcohol of the person's breathing air into carbon monoxide, selecting a predetermined quantity of the carbon monoxide with the treated breathing air, and passing the collected quantity through the detector to determine the quantity of carbon monoxide as an indicator of the alcohol content.

A further object of the invention is to provide a device for testing a person's breath for the determination of alcohol content which includes a testing tube through which the breath is directed first into heating means such as pyrolysis oven in order to form carbon monoxide of the alcohol and then passing the treated breathing air with the carbon monoxide into a collector to accumulate a predetermined quantity thereof and then passing the predetermined quantity through an indicator tube to indicate the carbon monoxide which is present therein.

A further object of the invention is to provide a device for testing a person's breath for alcohol content which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the Drawings:

FIG. 1 is a schematic view of a testing device in which breathing air is directed through a pyrolysis oven and carbon monoxide is formed which together with the treated air is passed into a collector; and FIG. 2 is a view showing the collector connection to a carbon monoxide test tube and pump for the purpose of passing the collector quantity through the test tube.

DESCRIPTION OF THE PREFERRED EMBODIMENTS

Referring to the drawings in particular, the invention embodied therein comprises a method of testing a person's breath for the purpose of determining its alcohol content as an indication of the alcohol in the person's blood. In accordance with the invention, a sample of expiratory breathing air 1 is directed through a mouthpiece 10 and a testing tube 12 through a pyrolysis oven or other heating device 2 in which the alcohol content of the breathing air is formed into carbon monoxide. The treated breathing air and the formed carbon monoxide are then passed through a continuation tube 14 to a collector 3 where a predetermined quantity of the treated breathing air and carbon monoxide is collected.

Thereafter, in accordance with the method the predetermined quantity in the collector 3 as shown in FIG. 2 is directed through a carbon monoxide test tube by sucking it through using a suction pump 5.

In accordance with the method of the invention the exhaled breath is blown by the person being tested through a conventional mouthpiece 10 of a tube 12 across the pyrolysis oven 2 into the collector 3, which advantageously comprises a plastic measuring bag. In the pyrolysis oven 2, heated to about 800° C., the ethyl alcohol is oxidized to CO with a high yield:

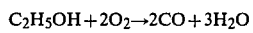

$$C_2H_5OH + 2O_2 \rightarrow 2CO + 3H_2O$$

The pyrolyzed breath sample is then sucked in known manner from the collector 3 through a CO test tube 4 by the bellows pump 5.

On the basis that, at 100% yield, 1 mol $C_2H_5OH$ produce 2 mol CO, as little as 2.5 ppm alcohol in the exhaled breath can still be detected by a known CO test tube having a measuring range from 5 to 150 ppm. The 2.5 ppm alcohol in the exhaled breath correspond to a blood alcohol concentration of 0.001%.

In accordance with a preferred embodiment of the invention, the breathing air is treated by heating it to a temperature of between 780° to 820° C.

While specific embodiments of the invention have been shown and described in detail to illustrate the application of the principles of the invention, it will be understood that the invention may be embodied otherwise without departing from such principles.

What is claimed is:

1. A method of testing a person's breath for the purpose of determining its alcohol content as an indication of the ethyl alcohol in the person's blood of the type using a colorimetric carbon monoxide gas detector tube, comprising obtaining a sample of expiratory breathing air of the person, conducting the sample through a pyrolysis oven and operating the pyrolysis oven to decompose the alcohol and form carbon monoxide, collecting a predetermined quantity of the pyrolized sample, and passing the collected quantity through the detector tube to determine the quantity of carbon monoxide as an indication of the alcohol content.

2. A method according to claim 1, wherein said pyrolyzing step comprises heating the sample to a temperature of between 780° and 820° C.

3. A method of testing a person's breath for the purpose of determining its alcohol content as an indication of the ethyl alcohol in the person's blood of the type using a colorimetric carbon monoxide gas detector tube, comprising obtaining a sample of expiratory breathing air of the person, conducting the sample through a pyrolysis oven and operating the pyrolysis oven to decompose the alcohol and form carbon monoxide, collecting a predetermined quantity of the pyrolyzed sample, passing the collected quantity through the detector tube to determine the quantity of carbon monoxide as an indication of the alcohol content, and wherein said pyrolyzing step comprises heating the sample to a temperature of between 780° and 820° C.

* * * * *